(12) United States Patent
Wang

(10) Patent No.: US 7,727,172 B2
(45) Date of Patent: Jun. 1, 2010

(54) BACK BRACE HAVING PULL CORD FOR SIZE ADJUSTMENT

(75) Inventor: Chih-Chuan Wang, Taichung County (TW)

(73) Assignee: Kao Chen Enterprise Co., Ltd., Taichung Hsien (TW)

( * ) Notice: Subject to any disclaimer, the term of this patent is extended or adjusted under 35 U.S.C. 154(b) by 122 days.

(21) Appl. No.: 12/034,240

(22) Filed: Feb. 20, 2008

(65) Prior Publication Data

US 2009/0118655 A1    May 7, 2009

(51) Int. Cl.
*A61F 5/00* (2006.01)
(52) U.S. Cl. ............................................. 602/19; 602/5
(58) Field of Classification Search ............... 602/5, 602/19; 2/336, 337, 319, 338, 467
See application file for complete search history.

(56) References Cited

U.S. PATENT DOCUMENTS 5,346,461 A    9/1994    Heinz et al.
6,213,968 B1 *    4/2001    Heinz et al. ................... 602/19
6,322,529 B1 *    11/2001    Chung .......................... 602/19
7,001,348 B2 *    2/2006    Garth et al. ..................... 602/5
2004/0139974 A1 *    7/2004    Schwenn et al. ............ 128/846

* cited by examiner

*Primary Examiner*—Michael A. Brown
(74) *Attorney, Agent, or Firm*—Browdy and Neimark, PLLC

(57) ABSTRACT

A back brace includes a first brace member having a first connector, and a second brace member having a second connector and a coupler at two opposite sides thereof. The coupler is detachably connectable to the first connector. A first adjustment holder is affixed to one end of the first brace member and holds therein a first rod member. A second adjustment holder is affixed to one end of the second brace member and holds therein a second rod member. Two pull cords are inserted through the first adjustment holder and the second adjustment holder and run alternately back and forth over the first rod member and the second rod member to adjustably and abuttably hold the first and second brace members side by side. Two fastening members are fastened to distal ends of the pull cords and detachably connectable to the first and second connectors.

4 Claims, 4 Drawing Sheets

US 7,727,172 B2

BACK BRACE HAVING PULL CORD FOR SIZE ADJUSTMENT

BACKGROUND OF THE INVENTION

1. Field of the Invention

The present invention relates to a back brace for supporting the back of a person and more particularly to a back brace having pull cords for size adjustment.

2. Description of the Related Art

A regular back brace is generally formed of a soft elastic belt for wearing around the waist or abdomen of a person and a tape of hook member and a tape of loop member of a hook and loop fastener respectively provided at two opposite sides of the soft elastic belt for securing the soft elastic belt to the body of a person. When the user wants to adjust the tightness of the soft elastic belt subject to the desired tension, the user must separate the tape of hook member and the tape of loop member, and then pull the soft elastic belt to the desired tightness, and then fasten the tape of hook member and the tape of loop member together. Directly pulling the soft elastic belt to the desired tightness requires much effort. This adjustment operation is somewhat difficult to an old person, woman or patient who does not have great strength.

To eliminate the aforesaid effort adjustment problem, back braces with electronic tension control means are developed. U.S. Pat. No. 5,346.461 discloses a similar design entitled "Electromechanical Back Brace Apparatus". According to this patent, the back brace apparatus has electromechanical means for tightening a brace around the trunk of a patient to a desired tension. The electromechanical means is controllable by the patient to effect predetermined tension settings. Further, a cable and pulley arrangement tightened by a motor provides a mechanical advantage so that the brace may be tightened by a small motor. A microprocessor controls the motor to obtain the desired repeatable tension settings. This design allows the user to adjust the back brace subject to the desired tension conveniently without much effort. However, the electromechanical means uses expensive electronic component parts, and has a complicated structure. Because of high sale price, this design of back brace apparatus cannot be popularly accepted.

SUMMARY OF THE INVENTION

The present invention has been accomplished under the circumstances in view. It is the primary objective of the present invention to provide a back brace, which allows adjustment of the tightness subject to the desired tension conveniently with less effort.

It is another objective of the present invention to provide a back brace, which has a simple structure and is inexpensive to manufacture.

To achieve these objectives of the present invention, the back brace provided by the present invention comprises first and second brace members, first and second adjustment holders, at least one pull cord, and two fastening members. The first brace member includes a first belt body and a first connector fixedly mounted on the first belt body. The second brace member includes a second belt body, a second connector mounted on the second belt body, and a coupler mounted on the second belt body opposite to the second connector and detachably connectable to the first connector. The first adjustment holder is mounted on the first belt body and holds a first rod member therein. The second adjustment holder is mounted on the second belt body and holds a second rod member therein. The pull cord is inserted through the first adjustment holder and the second adjustment holder and runs alternately back and forth over the first rod member and the second rod member to adjustably and abuttably hold the first and second brace members side by side. The pull cord has two opposite distal ends extending out of the first holder body and the second holder body. The fastening members are fastened to distal ends of the pull cord and detachably connectable to the first and second connectors respectively.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWING

The present invention will become more fully understood from the detailed description given herein below and the accompanying drawings which are given by way of illustration only, and thus are not limitative of the present invention, and wherein.

DETAILED DESCRIPTION OF THE INVENTION

Figure 1:
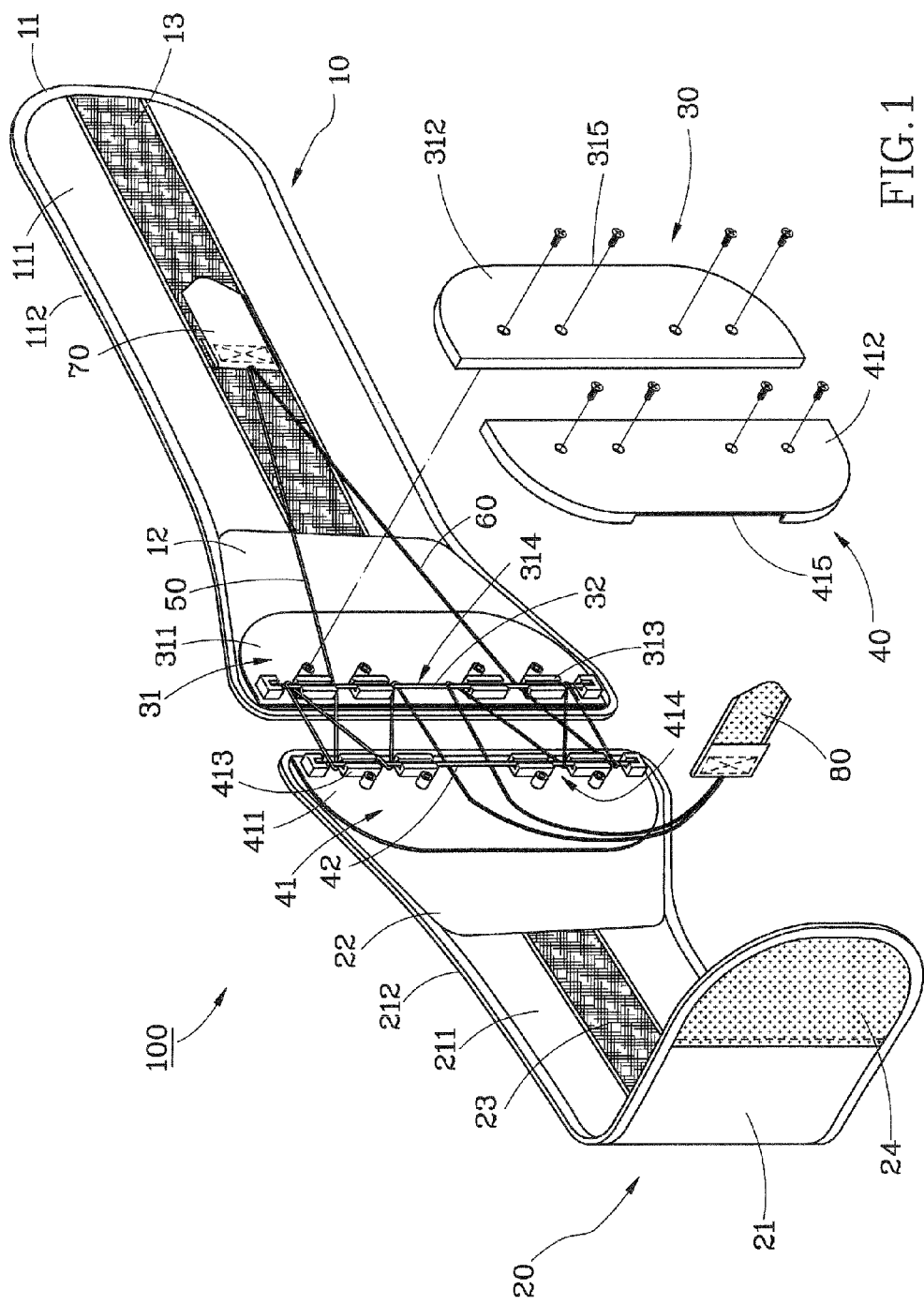
FIG. 1 is an exploded view of a back brace constructed in accordance with a preferred embodiment of the present invention.

Referring to FIGS. 1-4, a back brace 100 in accordance with a preferred embodiment of the present invention comprises a first brace member 10, a second brace member 20 a first adjustment holder 30, a second adjustment holder 40 two pull cords 50 and 60 and two fastening members 70 and 80.

The first brace member 10 comprises a first belt body 11, a first support plate 12, and a first connector 13. The first belt body 11 is made out of a soft, slightly elastic, flexible material, defining a first outer surface 111 and a first inner surface 112 opposite to the first outer surface 111. The first support plate 12 is a hard member fixedly fastened to the first outer surface 111 adjacent to one end of the first belt body 11. The first connector 13 is a tape of loop member of a hook and loop fastener fixedly mounted on and extending along the major axis of the first belt body 11.

The second brace member 20 comprises a second belt body 21, a second support plate 22, a second connector 23 and a coupler 24. The second belt body 21 is made out of a soft, slightly elastic, flexible material, defining a second outer surface 211 and a second inner surface 212 opposite to the second outer surface 211. The second support plate 22 is a hard member fixedly fastened to the second outer surface 211 adjacent to one end of the second belt body 21. The second connector 23 is a tape of loop member of a hook and loop fastener fixedly mounted on and extending along the major axis of the second belt body 21. The coupler 24 is a tape of hook member of a hook and loop fastener fixedly mounted on the second inner surface 212 of the second belt body 21 remote from the second support plate 22, and detachably connectable to the first connector 13 of the first brace member 10.

The first adjustment holder 30 comprises a first holder body 31 and a first rod member 32. The first holder body 31 includes a first bottom shell 311 and a first top cover shell 312. The first bottom shell 311 is fixedly bonded to the first support plate 12 of the first brace member 10. The first bottom shell 311 has a plurality of first protrusions 313 spacedly arranged in a line adjacent to one end of the first belt body 11. The first rod member 32 is a round rod supported on the first protrusions 313, thereby defining a plurality of first insertion holes 314 in between each two adjacent protrusions 313. The first top cover shell 312 is covered on the first bottom shell 311 so that the first rod member 32 is retained between the first bottom shell 311 and the first top cover shell 312. The first top cover shell 312 has a plurality of openings 315 disposed in communication with the first insertion holes 314.

The second adjustment holder 40 comprises a second holder body 41 and a second rod member 42. The second holder body 41 includes a second bottom shell 411 and a second top cover shell 412. The second bottom shell 411 is fixedly bonded to the second support plate 22 of the second brace member 20. The second bottom shell 411 has a plurality of second protrusions 413 spacedly arranged in a line adjacent to one end of the second belt body 21. The second rod member 42 is a round rod supported on the second protrusions 413, thereby defining a plurality of second insertion holes 414 in between each two adjacent protrusions 413. The second top cover shell 412 is covered on the second bottom shell 411 so that the second rod member 42 is retained between the second bottom shell 411 and the second top cover shell 412. The second top cover shell 412 has a plurality of openings 415 in communication with the second insertion holes 414.

One pull cord 50 is inserted through the first adjustment holder 30 and the second adjustment holder 40 and alternately running through the first insertion holes 314 on the upper half of the first brace member 10 and the second insertion holes 414 on the upper half of the second brace member 20 in a zigzag manner around the first rod member 32 and the second rod member 42, and the two distal ends of the pull cord 50 are respectively extending out of the openings 315 and 415 of the first and second adjustment holder 30 and 40. The other pull cord 60 is inserted through the first adjustment holder 30 and the second adjustment holder 40 and alternately running through the first insertion holes 314 on the lower half of the first brace member 10 and the second insertion holes 414 on the lower half of the second brace member 20 in a zigzag manner around the first rod member 32 and the second rod member 42, and the two distal ends of the pull cord 60 are respectively extending out of the openings 315 and 415 of the first and second adjustment holder 30 and 40.

The two fastening members 70 and 80 are tapes of hook member of a hook and loop fastener. One fastening member 70 is fixedly connected with the ends of the two pull cords 50 and 60 that extend out of the openings 315 of the first adjustment holder 30, and detachably connectable to the first connector 13 of the first brace member 10. The other fastening member 80 is fixedly connected with the ends of the two pull cords 50 and 60 that extend out of the openings 415 of the second adjustment holder 40, and detachably connectable to the second connector 23 of the second brace member 20.

After understanding of the structure of the component parts of the back brace 100 and their installation., the use and adjustment of the back brace 100 are described hereinafter.

Figure 2:
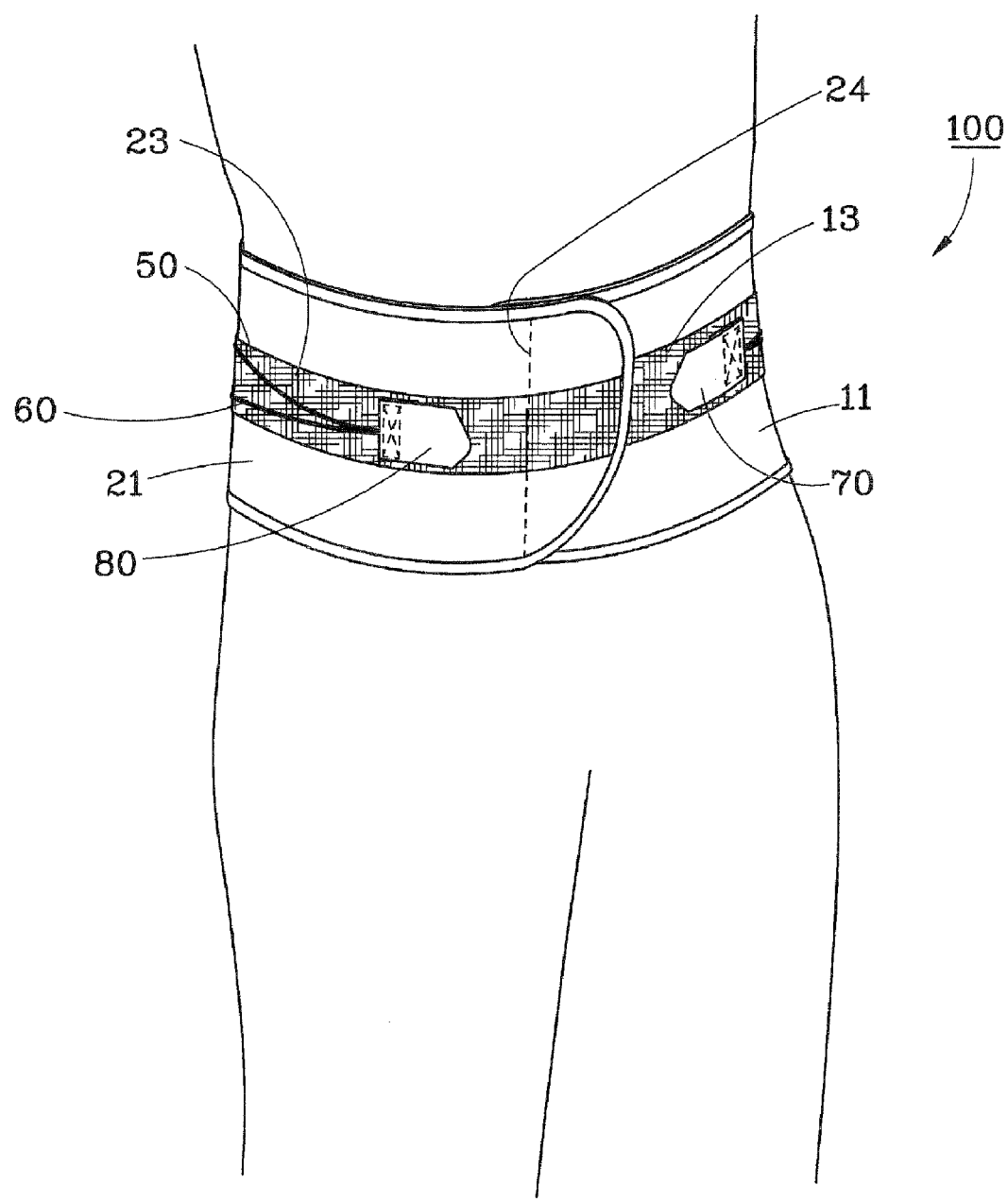
FIG. 2 is a schematic drawing showing the back brace wound round the waist of a person.

When the back brace 100 is used, as shown in FIG. 2, the first brace member 10 and the second brace member 20 are attached around the user's waist or abdomen, and the coupler 24 of the second brace member 20 is fastened to the first connector 13 of the first brace member 10, thereby securing the back brace 100 to the user's waist or abdomen and holding the first and second support plates 12 and 22 on the back side of the user's body to support the muscles of the user's back and to keep the user's lumbar spine in shape.

When adjusting the tightness of the back brace 100 after the back brace 100 is wound round the user's waist or abdomen, the user uses the two hands to detach the two fastening members 70 and 80 from the first and second connectors 13 and 14.

Figure 3:
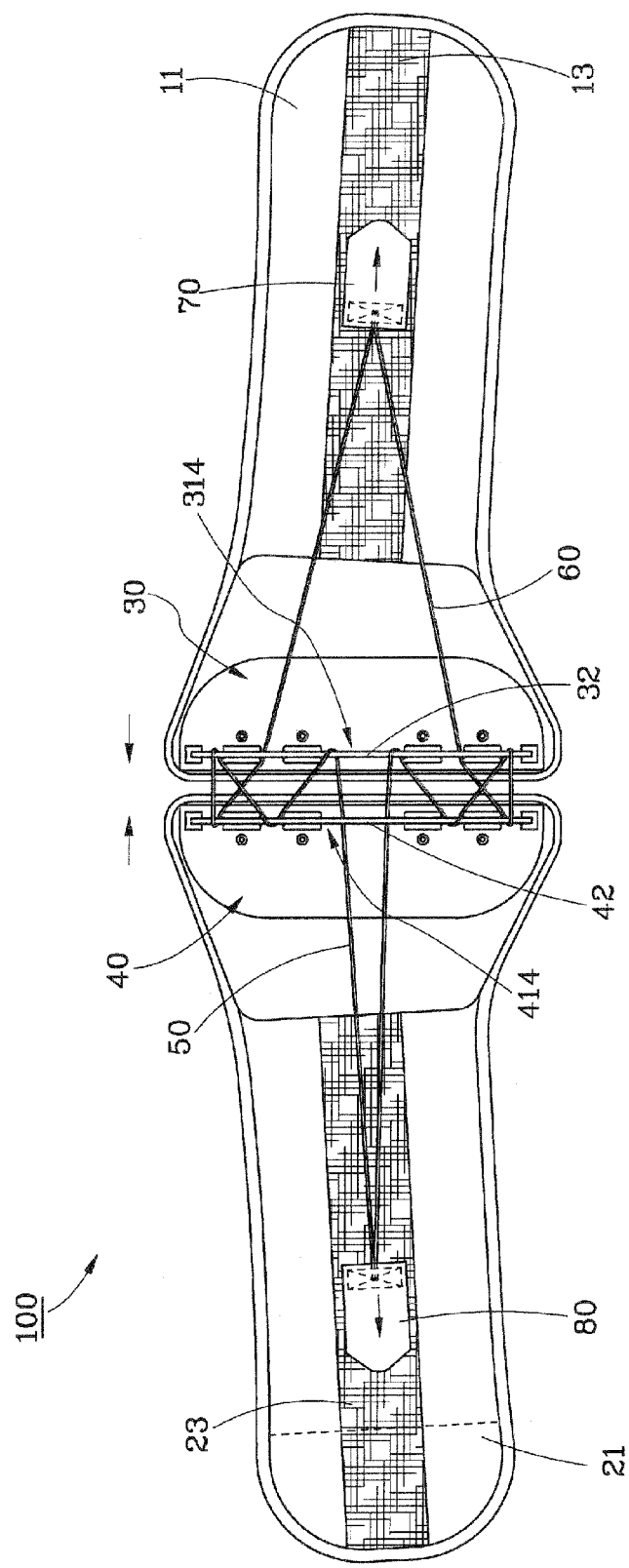
FIG. 3 is a schematic drawing showing tightening adjustment of the back brace in accordance with the preferred embodiment of the present invention.
Figure 4:
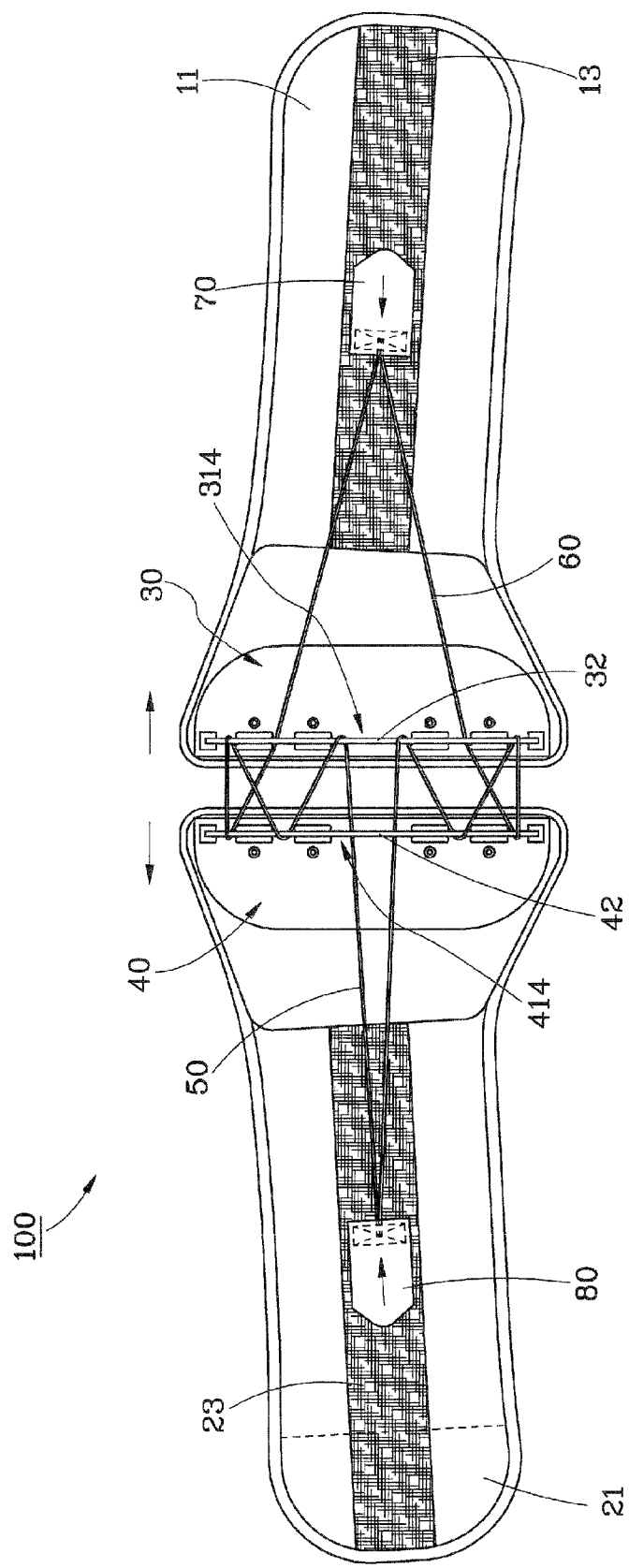
FIG. 4 is a schematic drawing showing loosening adjustment of the back brace in accordance with the preferred embodiment of the present invention.

When wanting to tighten the tightness of the back brace 100, as shown in FIG. 3, the user can pull the two fastening members 70 and 80 in direction away from the first and second adjustment holders 30 and 40 to stretch the two pull cords 50 and 60, causing the rod members 34 and 42 of the adjustment holders 30 and 40 to be moved toward each other subject to the desired tension and then the two fastening members 70 and 80 are respectively fastened to the first and second connectors 13 and 14. When wishing to loosen the tightness of the back brace 100 after disconnection of the two fastening members 70 and 80 from the first and second connectors 13 and 14, as shown in FIG. 4, the user can move the two fastening members 70 and 80 in direction toward the first and second adjustment holders 30 and 40 for allowing the first brace member 10 and the second brace member 20 to be pulled apart and then fasten the two fastening members 70 and 80 to the first and second connectors 13 and 14. By means of the aforesaid procedure, the user can conveniently adjust the tightness of the back brace 100.

As stated above, the two pull cords 50 and 60 extend over the first and second rod members 32 and 42 of the first and second adjustment holders 30 and 40 in a zigzag manner, and therefore the user can pull the pull cords 50 and 60 to move the first and second rod members 32 and 42 of the first and second adjustment holders 30 and 40 toward each other efficiently with less effort. Therefore an old person, woman or patient can adjust the tightness of the back brace 100 easily. Further, because the invention is a mechanical design, the manufacturing cost is low.

In the aforesaid preferred embodiment, two pull cords are used; however: this design is not a limitation. Alternatively, the back brace can be made using one single pull cord or more than two pull cords to achieve the same effect.

The invention being thus described it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A back brace comprising:
a first brace member including a first belt body made of a flexible material, and a first connector mounted on one side of said first belt body;
a second brace member including a second belt body made of a flexible material, a second connector mounted on a first side of said second belt body, and a coupler mounted on a second side of said second belt body opposite to first side of said second belt body and detachably connectable to said first connector of said first brace member;
a first adjustment holder including a first holder body mounted on said first belt body and provided at an inside thereof with a plurality of first protrusions spacedly arranged, and a first rod member supported on said first protrusions and defining with said first protrusions a plurality of first insertion holes, said first holder body having a plurality of openings in communication with said first insertion holes;

a second adjustment holder including a second holder body mounted on said second belt body and provided at an inside thereof with a plurality of second protrusions spacedly arranged, and a second rod member supported on said second protrusions and defining with said second protrusions a plurality of second insertion holes, said second holder body having a plurality of openings in communication with said second insertion holes;

at least one pull cord inserted through said first adjustment holder and said second adjustment holder and alternately running through said first insertion holes and said second insertion holes in a zigzag manner around said first rod member and said second rod member, said pull cord having two opposite ends respectively extending out of said first holder body and said second holder body; and two fastening members respectively affixed to the two opposite ends of said pull cord and detachably connectable to said first connector and said second connector.

2. The back brace as claimed in claim 1, wherein said first brace member further comprises a first hard support plate fixedly mounted on one side of said first belt body adjacent to one end of said first belt body for supporting the user's back; said second brace member further comprises a second hard support plate fixedly mounted on one side of said second belt body adjacent to one end of said second belt body for supporting the user's back.

3. The back brace as claimed in claim 1, wherein said first connector is a tape of loop member of a hook and loop fastener extending along a major axis of said first belt body; said second connector is a tape of loop member of a hook and loop fastener extending along a major axis of said second belt body; said coupler is a tape of hook member of a hook and loop fastener; said fastening members each are a tape of hook member of a hook and loop fastener.

4. The back brace as claimed in claim 1, wherein said first holder body comprises a first bottom shell and a first top cover shell, said first bottom shell being affixed to said first belt body and provided with said first protrusions, said first cover shell being covered on said first bottom shell to hold said first rod member on said first protrusions between said first bottom shell and said first top cover shell, said first cover shell defining the openings of said first holder body; said second holder body comprises a second bottom shell and a second top cover shell, said second bottom shell being affixed to said second belt body and provided with said second protrusions, said second cover shell being covered on said second bottom shell to hold said second rod member on said second protrusions between said second bottom shell and said second top cover shell, said second cover shell defining the openings of said second holder body.

* * * * *